United States Patent [19]

Koshihara et al.

[11] Patent Number: 4,886,370
[45] Date of Patent: * Dec. 12, 1989

[54] METHOD FOR DETECTING A STATE OF SUBSTANCE EXISTING IN PIPE

[75] Inventors: Toshio Koshihara; Rokurou Misawa; Yuzo Sagawa; Kimio Takehara, all of Tokyo, Japan

[73] Assignee: NKK Corporation, Tokyo, Japan

[ * ] Notice: The portion of the term of this patent subsequent to Oct. 10, 2006 has been disclaimed.

[21] Appl. No.: 229,835

[22] Filed: Aug. 8, 1988

[30] Foreign Application Priority Data

Aug. 25, 1987 [JP] Japan ............................. 62-209311
Mar. 18, 1988 [JP] Japan ............................... 63-64820

[51] Int. Cl.$^4$ ........................................... G01N 25/72
[52] U.S. Cl. ........................................ 374/5; 374/44;
374/124; 374/141; 374/137; 250/330; 356/43;
358/100; 358/107; 358/113
[58] Field of Search .................... 374/5, 30, 44, 137,
374/106, 124, 50, 141, 17; 358/113, 100, 107,
113; 250/330; 356/43, 51

[56] References Cited

U.S. PATENT DOCUMENTS

| | | | |
|---|---|---|---|
| 3,504,524 | 4/1970 | Maley | 374/124 |
| 3,566,669 | 3/1971 | Lawrence et al. | 374/124 |
| 4,395,380 | 7/1983 | Rosh | 374/124 |

OTHER PUBLICATIONS

McLaughlin, P. V. et al., "Non-Destructive Examination of Fibre Composite Structures by Thermal Field Techniques", NDT International, Apr. 1980, pp. 56–62.

*Primary Examiner*—William A. Cuchlinski, Jr.
*Assistant Examiner*—Diego F. F. Gutierrez
*Attorney, Agent, or Firm*—Frishauf, Holtz, Goodman & Woodward

[57] ABSTRACT

A method for detecting a state of a substance existing in a pipe, the outer surface of which is exposed, which comprises: heating or cooling a pipe, the outer surface of which is exposed, from the side of the outer surface thereof so that a difference in temperature is produced between a portion of the outer surface of the pipe corresponding to a portion of the inner surface thereof, which is in contact with a solid or liquid substance existing in the pipe, and a portion of the outer surface of the pipe corresponding to a portion of the inner surface thereof, which is not in contact with the substance; then shooting the outer surface of the pipe by means of a thermal imaging system while the above-mentioned difference in temperature still remains on the outer surface of the pipe to obtain a thermal image of the difference in temperature; and detecting a state of the substance existing in the pipe by means of the thus obtained thermal image.

6 Claims, 7 Drawing Sheets

FIG. 3(A)
FIG. 3(B)
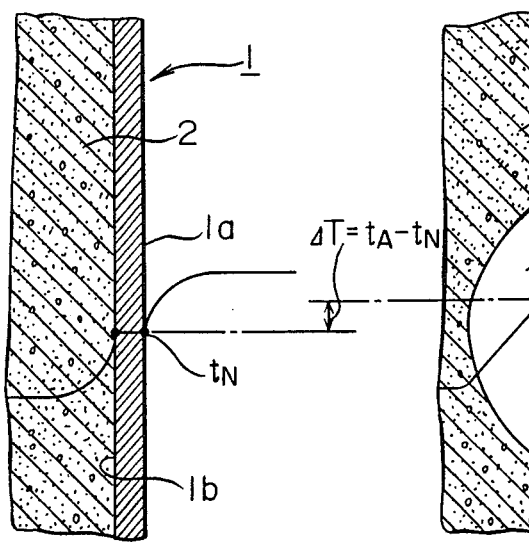
FIG. 4
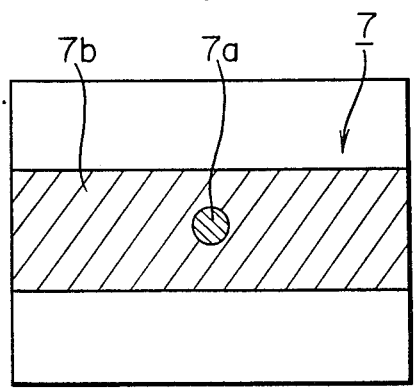

FIG. 5
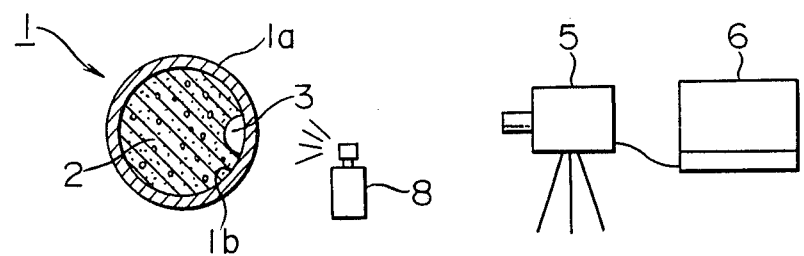
FIG. 6(A)    FIG. 6(B)
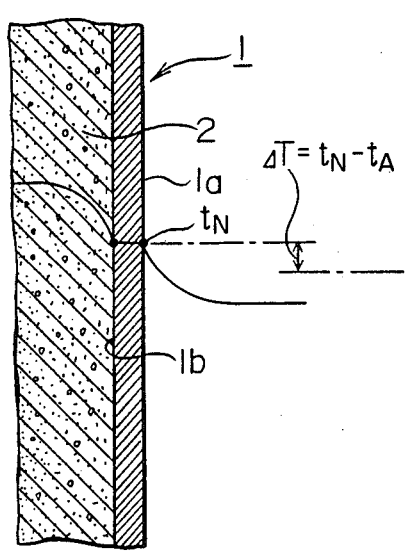
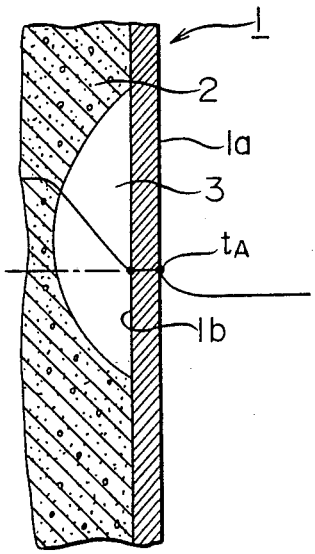

METHOD FOR DETECTING A STATE OF SUBSTANCE EXISTING IN PIPE

FIELD OF THE INVENTION

The present invention relates to a method for detecting a state of a solid or liquid substance existing in a pipe, the outer surface of which is exposed.

BACKGROUND OF THE INVENTION

It is often necessary to detect the following state of a solid or liquid substance existing in a pipe, the outer surface of which is exposed:

(1) In a pipe charged with concrete, a state of charging of said concrete;

(2) In a pipe serving as a trough in a plant building, a state of accumulation of dust;

(3) In a pipe in which a liquid exists, a level of the surface of said liquid; and (4) In a pipe having a neck portion where the cross-sectional area of the pipe is sharply reduced, and through which a liquid is flowing, a position of occurrence of a cavity at said neck portion.

The following methods are known for detecting a state of charging of concrete in a pipe charged with concrete, or state of accumulation of dust in a pipe serving as a trough:

(A) Detecting method using radioactive rays:

This method comprises: projecting radioactive rays such as X-ray or gamma-ray toward a pipe to be tested from the side of the outer surface thereof, measuring an amount of radioactive rays having passed through the pipe, and detecting a state of charging of concrete in the pipe or a state of accumulation of dust in the pipe by means of the thus measured amount of transmission of the radioactive rays.

(B) Detecting method using ultrasonic waves:

This method comprises: transmitting ultrasonic waves toward a pipe to be tested from the side of the outer surface thereof, receiving reflected waves of the transmitted ultrasonic waves, measuring a period of time required up to receiving of the reflected waves of the transmitted ultrasonic waves, and detecting a state of charging of concrete in the pipe or a state of accumulation of dust in the pipe by means of the period of time required up to receiving of the reflected waves.

(C) Detecting method based on knocking:

This method comprises: knocking a pipe to be tested from the side of the outer surface thereof with a hammer, for example, and detecting a state of charging of concrete in the pipe or a state of accumulation of dust in the pipe by means of the thus produced sound.

(D) Detecting method based on cutting:

This method comprises: cutting out a pipe to be tested to permit an operator to observe directly the inner surface of the pipe, thereby detecting a state of accumulation of dust in the pipe.

The detecting method using radioactive rays as mentioned in (A) above has the following problems:

(a) Detecting operation cannot be conducted unless the operator is qualified for handling radioactive rays. There is therefore a limitation in personnel.

(b) It is difficult to make a proper judgement on the result of detection, requiring high-level experience and technical knowledge.

(c) Detecting operation can be carried out only at a position closest to the outer surface of the pipe. When the pipe is installed at an elevated position apart from the ground, therefore, it is necessary to provide a scaffold for detecting operation.

(d) The range of a single run of detection is narrow. It thus requires much time and labor for detecting operation, leading to a low operating efficiency.

The detecting method using ultrasonic waves as mentioned in (B) above has the following problems:

(a) An error is often contained in the result of detection, thus preventing accurate detection.

(b) Detecting operation can be carried out only at a position in contact with the outer surface of the pipe. When the pipe is installed at an elevated position apart from the ground, therefore, it is necessary to provide a scaffold for detecting operation.

(c) The range of a single run of detection, being only a point, is very narrow. It thus requires much time and labor for detecting operation, leading to a low operating efficiency.

The detecting method based on knocking as mentioned in (C) above has the following problems:

(a) Determination of a state of a substance existing in the pipe requires high-level experience and technical knowledge, with furthermore much differences between individual operators, thus impairing accurate detection of a state of the substance existing in the pipe.

(b) Detecting operation can be carried out only at a position closest to the outer surface of the pipe. When the pipe is installed at an elevated position apart from the ground, therefore, it is necessary to provide a scaffold for detecting operation.

(c) Detecting operation requires much time and labor, resulting in a low operating efficiency.

The detecting method based on cutting as mentioned in (D) above has the following problems:

(a) Use of the pipe must be interrupted for a while during cutting and detecting operations, and these cutting, detecting and restoring operations require much time and labor, resulting in a low operating efficiency.

(b) When the pipe is installed at an elevated position apart from the ground, it is necessary to provide a scaffold for detecting operation.

For a pipe, having a neck portion where the cross-sectional area of the pipe is sharply reduced, and through which a liquid is flowing, a method is known for detecting a position of occurrence of a cavity at the neck portion, which comprises: receiving ultrasonic waves produced upon disappearance of a cavity produced at the neck portion of the pipe by means of an underwater microphone installed in the pipe, and detecting a position of occurrence of the cavity by means of an acoustic pressure level of the thus received ultrasonic waves.

The abovementioned method for detecting the cavity has the following problems:

(a) It is difficult to make a proper judgement on the result of detection, requiring high-level experience and technical knowledge.

(b) An accurate position of occurrence of the cavity cannot be detected, and it is impossible to detect an accurate magnitude of the cavity.

(c) The underwater microphone installed in the pipe impairs smooth flow of the liquid through the pipe.

An appropriate method for detecting a level of the surface of a liquid existing in a pipe is not known.

Under such circumstances, there is a strong demand for development of a method which permits certain, easy and efficient detection of a state of a solid or liquid substance existing in a pipe, the outer surface of which is exposed, at a position apart from the pipe in a non-contact manner without the need for a special qualification, but a method provided with such properties has not as yet been proposed.

SUMMARY OF THE INVENTION

An object of the present invention is therefore to provide a method which permits certain, easy and efficient detection of a state of a solid or liquid substance existing in a pipe, the outer surface of which is exposed, at a position apart from the pipe in a non-contact manner without the need for a special qualification.

In accordance with one of the features of the present invention, there is provided a method for detecting a state of a substance existing in a pipe, the outer surface of which is exposed, comprising:

heating or cooling a pipe, the outer surface of which is exposed, from the side of the outer surface thereof so that a difference in temperature is produced between a portion of the outer surface of said pipe corresponding to a portion of the inner surface thereof, which is in contact with a solid or liquid substance existing in said pipe, and a portion of the outer surface of said pipe corresponding to a portion of the inner surface thereof which is not in contact with said substance; then shooting the outer surface of said pipe by means of a thermal imaging system while said difference in temperature still remains on the outer surface of said pipe to obtain a thermal image of said difference in temperature; and detecting a state of said substance existing in said pipe by means of the thus obtained thermal image.

BRIEF DESCRIPTION OF THE DRAWINGS

FIG. 3 (A) is a descriptive view illustrating a temperature of a portion of the outer surface of a pipe corresponding to a portion of the inner surface thereof, which is in contact with concrete charged in the pipe, when the pipe has been heated from the side of the outer surface thereof in accordance with the first embodiment of the method of the present invention as shown in FIG. 1;

FIG. 3 (B) is a descriptive view illustrating a temperature of a portion of the outer surface of a pipe corresponding to a portion of the inner surface thereof, which is not in contact with concrete charged in the pipe, when the pipe has been heated from the side of the outer surface thereof in accordance with the first embodiment of the method of the present invention as shown in FIG. 1;

FIG. 4 is a descriptive view illustrating a typical thermal image shot in accordance with the first embodiment of the method of the present invention as shown in FIG. 1;

FIG. 5 is a schematic descriptive side view illustrating a second embodiment of the method of the present invention;

FIG. 6 (A) is a descriptive view illustrating a temperature of a portion of the outer surface of a pipe corresponding to a portion of the inner surface thereof, which is in contact with concrete charged in the pipe, when the pipe has been cooled from the side of the outer surface thereof in accordance with the second embodiment of the method of the present invention as shown in FIG. 5;

FIG. 6 (B) is a descriptive view illustrating a temperature of a portion of the outer surface of a pipe corresponding to a portion of the inner surface thereof, which is not in contact with concrete charged in the pipe, when the pipe has been cooled from the side of the outer surface thereof in accordance with the second embodiment of the method of the present invention as shown in FIG. 5;

DETAILED DESCRIPTION OF PREFERRED EMBODIMENTS

From the abovementioned point of view, extensive studies were carried out to develop a method which permits certain, easy and efficient detection of a state of a solid or liquid substance existing in a pipe, the outer surface of which is exposed, at a position apart from the pipe in a non-contact manner without the need for a special qualification. As a result, the following finding was obtained:

For example, a pipe to be tested, in which a solid or liquid substance exists, is heated or cooled for a certain period of time from the side of the outer surface thereof. In the case where there exists a portion of the inner surface of the pipe, which is not in contact with the aforementioned substance, in other words, there exists a vacant space in the pipe, the vacant space has a thermal conductivity lower than that of the aforementioned substance existing in the pipe. A difference in temperature is therefore produced between a portion of the outer surface of the pipe corresponding to a portion of the inner surface thereof, which is in contact with the substance, on the one hand, and a portion of the outer surface of the pipe corresponding to a portion of the inner surface thereof, which is not in contact with the substance, on the other hand. By shooting the outer surface of the pipe by means of a thermal imaging system, while this difference in temperature still remains on the outer surface of the pipe, to obtain a thermal image of the abovementioned difference in temperature, it is possible to detect a state of the aforementioned substance existing in the pipe by means of the thus obtained thermal image.

The present invention was developed on the basis of the above mentioned finding. Now, the method for detecting a state of a substance existing in a pipe of the present invention is described with reference to drawings.

Figure 1:
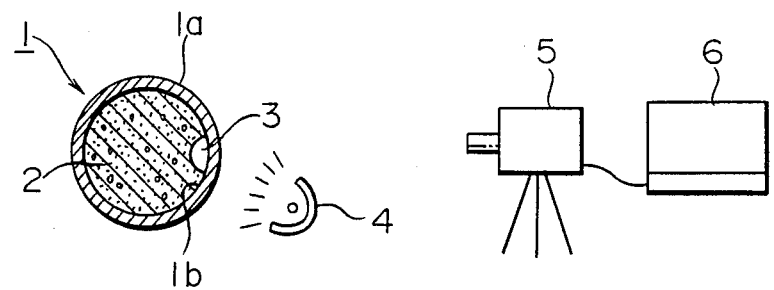
FIG. 1 is a schematic descriptive side view illustrating a first embodiment of the method of the present invention.
Figure 2:
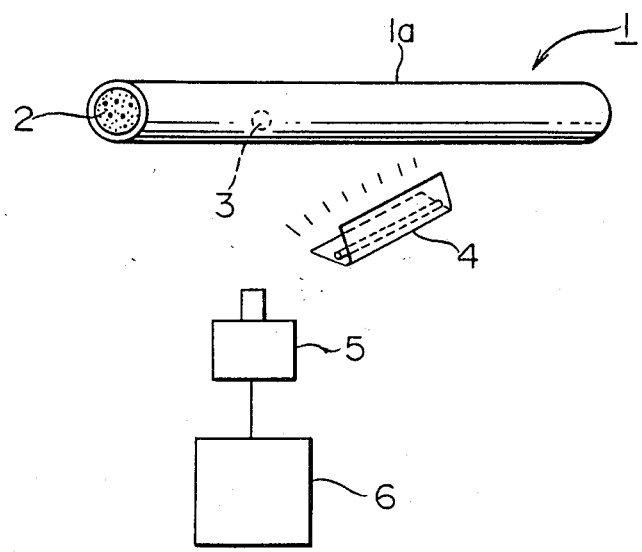
FIG. 2 is a schematic descriptive plan view illustrating the first embodiment of the method of the present invention as shown in FIG. 1.

FIG. 1 is a schematic descriptive side view illustrating a first embodiment of the method of the present invention; and FIG. 2 is a schematic descriptive plan view illustrating the first embodiment of the method of the present invention as shown in FIG. 1. As shown in FIGS. 1 and 2, in the first embodiment of the method of the present invention, concrete 2 as the aforementioned substance is previously charged in a pipe 1 to be tested, the outer surface 1a of which is exposed. The pipe 1 is heated from the side of the outer surface 1a thereof by means of a heating mechanism 4 so that a difference in temperature is produced between a portion of the outer surface 1a of the pipe 1 corresponding to a portion of the inner surface 1b thereof, which is in contact with the charged concrete 2, on the one hand, and a portion of the outer surface 1a of the pipe 1 corresponding to a portion of the inner surface 1b thereof, which is not in contact with the charged concrete 2, in other words, corresponding to a vacant space 3 in the pipe 1, on the other hand.

FIG. 3 (A) is a descriptive view illustrating a temperature of a portion of the outer surface 1a of the pipe 1 corresponding to a portion of the inner surface 1b thereof, which is in contact with the charged concrete 2 in the pipe 1, when the pipe 1 has been heated from the side of the outer surface 1a thereof in accordance with the first embodiment of the method of the present invention; and FIG. 3 (B) is a descriptive view illustrating a temperature of a portion of the outer surface 1a of the pipe 1 corresponding to a portion of the inner surface 1b thereof, which is not in contact with the charged concrete 2 in the pipe 1, in other words, corresponding to the vacant space 3 in the pipe 1, when the pipe 1 has been heated as described above. The vacant space 3 in the pipe 1 has a thermal conductivity lower than that of the charged concrete 2 in the pipe 1. Accordingly, because of the presence of the vacant space 3 having the lower thermal conductivity, a temperature of the portion of the outer surface 1a of the pipe 1 corresponding to the vacant space 3 increases, under the effect of the above mentioned heating, more rapidly than that of the portion of the outer surface 1a of the pipe 1 corresponding to the portion of the inner surface 1b thereof, which is in contact with the charged concrete 2. As a result, as shown in FIGS. 3 (A) and 3(B), the temperature $t_A$ of the portion of the outer surface 1a corresponding to the vacant space 3 is higher by $\Delta T$ than the temperature $t_N$ of the portion of the outer surface 1a corresponding to the Portion of the inner surface 1b, which is in contact with the charged concrete 2, after heating for a certain period of time.

While the above mentioned difference in temperature $\Delta T$ still remains on the outer surface 1a of the pipe 1, the outer surface 1a of the pipe 1 is shot by means of a thermal imaging system 5 to obtain a thermal image of the difference in temperature $\Delta T$, which has a portion showing a higher temperature, corresponding to the portion of the inner surface 1b of the pipe 1, which is not in contact with the charged concrete 2, in other words, corresponding to the vacant space 3 in the pipe 1. The thus obtained thermal image is displayed on a monitor TV screen 6. It is therefore possible to detect a state of charging of concrete 2 in the pipe 1 by means of the above mentioned thermal image. FIG. 4 is a descriptive view illustrating a typical thermal image 7 shot in the manner as described above. As shown in FIG. 4, the thermal image 7 of the outer surface 1a of the pipe 1 has a portion 7a showing a higher temperature, corresponding to the portion of the inner surface 1b of the pipe 1, which is not in contact with the charged concrete 2, in other words, corresponding to the vacant space 3 in the pipe 1, and a portion 7b showing a lower temperature, corresponding to the portion of the inner surface 1b of the pipe 1, which is in contact with the charged concrete 2. These portions 7a and 7b of the thermal image 7 are distinguishably indicated by colors predetermined for the respective ranges of temperature. More specifically, the portion 7a showing a relatively higher temperature is different in color from the portion 7b showing a relatively lower temperature. Therefore, it is possible to detect a position, a shape and an approximate size of the vacant space 3 in the pipe 1 by means of the portion 7a showing a higher temperature of the thermal image 7 shown in FIG. 4. It is thus possible to detect a state of charging of concrete 2 in the pipe 1.

The heating mechanism 4 capable of rapidly heating the pipe 1 within a short period of time, such as an infrared heater, should preferably be employed. When heating the pipe 1 from the side of the outer surface 1a thereof by means of the heating mechanism 4 and shooting the outer surface 1a of the pipe 1 by means of the thermal imaging system 5, it is necessary to heat the pipe 1 from the side of the outer surface 1a thereof for such a period of time as to produce the above mentioned difference in temperature $\Delta T$ between the portion of the outer surface 1a of the pipe 1 corresponding to the portion of the inner surface 1b thereof, which is in contact with the charged concrete 2, on the one hand, and the portion of the outer surface 1a of the pipe 1 corresponding to the portion of the inner surface 1b thereof, which is not in contact with the charged concrete 2, in other words, corresponding to the vacant space 3 in the pipe 1, on the other hand, and to shoot the outer surface 1a of the pipe 1 by means of the thermal imaging system 5 while the above mentioned difference in temperature $\Delta T$ still remains on the outer surface 1a of the pipe 1. The difference in temperature $\Delta T$ becomes almost null if the period of time for heating and for shooting after the end of heating exceeds a certain duration, thus making it impossible to detect the portion of the inner surface 1b of the pipe 1, which is not in contact with the charged concrete 2, i.e., the vacant space 3 in the pipe 1. The above mentioned heating time should therefore be appropriately set with reference to the diameter and the thickness of the pipe 1, the range of heating of the outer surface 1a thereof and the performance of the thermal imaging system 5.

FIG. 5 is a schematic descriptive side view illustrating a second embodiment of the method of the present invention. As shown in FIG. 5, in the second embodiment of the method of the present invention, concrete 2 as the aforementioned substance is previously charged in a pipe 1 to be tested, the outer surface 1a of which is exposed. The pipe 1 is cooled by means of a cooling mechanism 8 from the side of the outer surface 1a thereof so that a difference in temperature is produced between a portion of the outer surface 1a of the pipe 1 corresponding to a portion of the inner surface 1b thereof, which is in contact with the charged concrete 2, on the one hand, and a portion of the outer surface 1a of the pipe 1 corresponding to a portion of the inner surface 1b thereof, which is not in contact with the charged concrete 2, in other words, corresponding to the vacant space 3 in the pipe 1, on the other hand.

FIG. 6 (A) is a descriptive view illustrating a temperature of a portion of the outer surface 1a of the pipe 1 corresponding to a portion of the inner surface 1b thereof, which is in contact with the charged concrete 2 in the pipe 1, when the pipe 1 has been cooled from the side of the outer surface 1a thereof in accordance with the second embodiment of the method of the present invention; and FIG. 6 (B) is a descriptive view illustrating a temperature of a portion of the outer surface 1a of the pipe 1 corresponding to a portion of the inner surface 1b thereof, which is not in contact with the charged concrete 2 in the pipe 1, in other words, corresponding to the vacant space 3 in the pipe 1, when the pipe 1 has been cooled as described above. As described above, the vacant space 3 in the pipe 1 has a thermal conductivity lower than that of the charged concrete 2. Accordingly, because of the presence of the vacant space 3 having a lower thermal conductivity, a temperature of the portion of the outer surface 1a of the pipe 1 corresponding to the vacant space 3 decreases, under the effect of the above mentioned cooling, more rapidly than that of the portion of the outer surface 1a of the pipe 1 corresponding to the portion of the inner surface 1b thereof, which is in contact with the charged concrete 2. As a result, as shown in FIGS. 6 (A) and 6 (B), the temperature $t_A$ of the portion of the outer surface 1a corresponding to the vacant space 3 is lower by $\Delta T$ than the temperature $t_N$ of the portion of the outer surface 1a corresponding to the portion of the inner surface 1b, which is in contact with the charged concrete 2, after cooling for a certain period of time.

While the above mentioned difference in temperature $\Delta T$ still remains on the outer surface 1a of the pipe 1, the outer surface 1a of the pipe 1 is shot by means of a thermal imaging system 5 to obtain a thermal image of the difference in temperature $\Delta T$, which has a portion showing a lower temperature, corresponding to the portion of the inner surface 1b of the pipe 1, which is not in contact with the charged concrete 2, in other words, corresponding to the vacant space 3 in the pipe 1. The thus obtained thermal image is displayed on a monitor TV screen 6. It is therefore possible to detect a state of charging of concrete 2 in the pipe 1 by means of the above mentioned thermal image. More specifically, it is possible to detect a position, a shape and an approximate size of the vacant space 3 in the pipe 1 by means of the portion showing a lower temperature of the thermal image. It is thus possible to detect a state of charging of concrete 2 in the pipe 1.

Cooling of the pipe 1 from the side of the outer surface 1a thereof is accomplished by spraying a cooling medium onto the outer surface 1a of the pipe 1 by means of a cooling mechanism 8. An applicable cooling medium includes, in addition to water and air, a freon-based liquefied gas such as trifluorotrichlorethane and a low-boiling-point liquid such as acetone, ether or alcohol. When the abovementioned liquefied gas or a low-boiling-point liquid as the cooling medium is sprayed onto the outer surface 1a of the pipe 1, the sprayed liquefied gas or low-boiling-point liquid rapidly evaporates and takes evaporation heat. The outer surface 1a of the pipe 1 is therefore rapidly cooled, thus permitting rapid detection of the portion of the inner surface 1b of the pipe 1, which is not in contact with the charged concrete 2, i.e., the vacant space 3 of the pipe 1, by means of the thermal imaging system 5.

When cooling the pipe 1 from the side of the outer surface 1a thereof by means of the cooling mechanism 8 and shooting the outer surface 1a of the pipe 1 by means of the thermal imaging system 5, it is necessary to cool the pipe 1 from the side of the outer surface 1a thereof for such a period of time as to produce the above mentioned difference in temperature $\Delta T$ between the portion of the outer surface 1a of the pipe 1 corresponding to the portion of the inner surface 1b thereof, which is in contact with the charged concrete 2, on the one hand, and the portion of the outer surface 1a of the pipe 1 corresponding to the portion of the inner surface 1b thereof, which is not in contact with the charged concrete 2, in other words, corresponding to the vacant space 3 in the pipe 1, on the other hand, and to shoot the outer surface 1a of the pipe 1 by means of the thermal imaging system 5 while the above mentioned difference in temperature $\Delta T$ still remains on the outer surface 1a of the pipe 1. The difference in temperature $\Delta T$ becomes almost null if the period of time for cooling and for shooting after the end of cooling exceeds a certain duration, thus making it impossible to detect the portion of the inner surface 1b of the pipe 1, which is not in contact with the charged concrete 2, i.e., the vacant space 3 in the pipe 1. The above mentioned cooling time should therefore be appropriately set with reference to the diameter and the thickness of the pipe 1, the range of cooling of the outer surface 1a thereof and the performance of the thermal imaging system 5.

Figure 7:
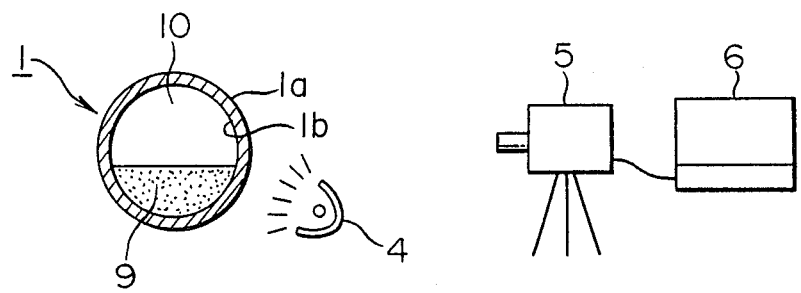
FIG. 7 is a schematic descriptive side view illustrating a third embodiment of the method of the present invention.

FIG. 7 is a schematic descriptive side view illustrating a third embodiment of the method of the present invention. As shown in FIG. 7, in the third embodiment of the method of the present invention, a pipe 1 to be tested, the outer surface 1a of which is exposed, is a pipe serving as a trough in a plant building, and dust 9 as the aforementioned substance is accumulated in the pipe 1. The pipe 1 is heated from the side of the outer surface 1a thereof by means of a heating mechanism 4 so that a difference in temperature is produced between a portion of the outer surface 1a of the pipe 1 corresponding to a portion of the inner surface 1b thereof, which is in contact with the accumulated dust 9, on the one hand, and a portion of the outer surface 1a of the pipe 1 corresponding to a portion of the inner surface 1b thereof, which is not in contact with the accumulated dust 9, in other words, corresponding to a vacant space 10 in the pipe 1, on the other hand.

The vacant space 10 in the pipe 1 has a thermal conductivity lower than that of the accumulated dust 9 in the pipe 1. Accordingly, because of the presence of the vacant space 10 having the lower thermal conductivity, a temperature of the portion of the outer surface 1a of the pipe 1 corresponding to the vacant space 10 increases, under the effect of the above mentioned heating, more rapidly than that of the portion of the outer surface 1a of the pipe 1 corresponding to the portion of the inner surface 1b thereof, which is in contact with the accumulated dust 9. As a result, the temperature $t_A$ of the portion of the outer surface 1a corresponding to the vacant space 10 is higher by $\Delta T$ than the temperature $t_N$ of the portion of the outer surface 1a corresponding to the portion of the inner surface 1b, which is in contact with the accumulated dust 9, after heating for a certain period of time.

Figure 8:
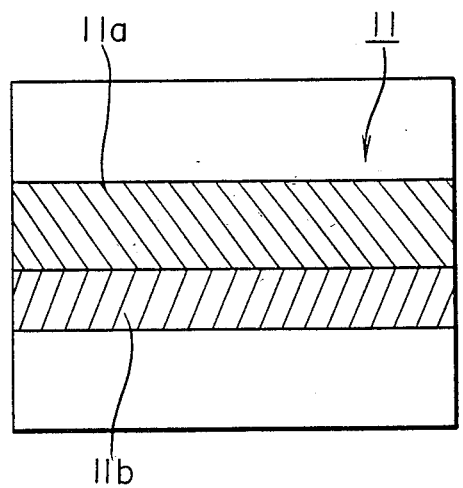
FIG. 8 is a descriptive view illustrating a typical thermal image shot in accordance with the third embodiment of the method of the present invention as shown in FIG. 7.

While the above mentioned difference in temperature ΔT still remains on the outer surface 1a of the pipe 1, the outer surface 1a of the pipe 1 is shot by means of a thermal imaging system 5 to obtain a thermal image of the difference in temperature ΔT, which has a portion showing a higher temperature, corresponding to the portion of the inner surface 1b of the pipe 1, which is not in contact with the accumulated dust 9, in other words, corresponding to the vacant space 10 in the pipe 1. The thus obtained thermal image is displayed on a monitor TV screen 6. It is therefore possible to detect a state of accumulation of the dust 9 in the pipe 1 by means of the above mentioned thermal image. FIG. 8 is a descriptive view illustrating a typical thermal image 11 shot in the manner as described above. As shown in FIG. 8, the thermal image 11 of the outer surface 1a of the pipe 1 has a portion 11a showing a higher temperature, corresponding to the portion of the inner surface 1b of the pipe 1, which is not in contact with the accumulated dust 9, in other words, corresponding to the vacant space 10 in the pipe 1, and a portion 11b showing a lower temperature, corresponding to the portion of the inner surface 1b of the pipe 1, which is in contact with the accumulated dust 9. These portions 11a and 11b of the thermal image 11 are distinguishably indicated by colors predetermined for the respective ranges of temperature. More specifically, the portion 11a showing a relatively higher temperature is different in color from the portion 11b showing a relatively lower temperature. Therefore, it is possible to detect a position, a shape and an approximate size of the vacant space 10 in the pipe 1 by means of the portion 11a showing a higher temperature of the thermal image 11 shown in FIG. 8, and to detect the portion of the inner surface 1b of the pipe 1, which is in contact with the accumulated dust 9, by means of the portion 11b showing a lower temperature of the thermal image 11. It is thus possible to detect a state of accumulation of the dust 9 in the pipe 1.

In the above mentioned third embodiment of the method of the present invention, by causing the accumulated dust 9 in the pipe 1 to contain previously cold water, it is possible to emphatically produce the above mentioned difference in temperature ΔT between the portion of the outer surface 1a of the pipe 1 corresponding to the portion of the inner surface 1b thereof, which is in contact with the accumulated dust 9, on the one hand, and the portion of the outer surface 1a of the pipe 1 corresponding to the portion of the inner surface 1b thereof, which is not in contact with the accumulated dust 9, in other words, corresponding to the vacant space 10 in the pipe 1, on the other hand. By shooting the outer surface 1a of the pipe 1 by means of the thermal imaging system 5 while the thus emphatically produced difference in temperature ΔT still remains on the outer surface 1a of the pipe 1, it is possible to detect more accurately the state of accumulation of the dust 9 in the pipe 1 in the form of a further clearer thermal image showing the difference in temperature ΔT.

Figure 9:
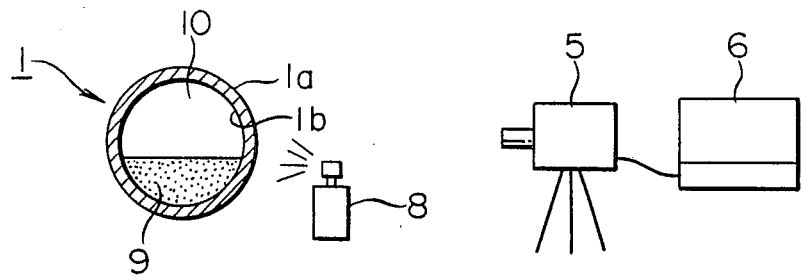
FIG. 9 is a schematic descriptive side view illustrating a fourth embodiment of the method of the present invention.

FIG. 9 is a schematic descriptive side view illustrating a fourth embodiment of the method of the present invention. As shown in FIG. 9, in the fourth embodiment of the method of the present invention, a pipe 1 to be tested, the outer surface 1a of which is exposed, is a pipe serving as a trough in a plant building, and dust 9 as the aforementioned substance is accumulated in the pipe 1. The pipe 1 is cooled from the side of the outer surface 1a thereof by means of a cooling mechanism 8 so that a difference in temperature is produced between a portion of the outer surface 1a of the pipe 1 corresponding to a portion of the inner surface 1b thereof, which is in contact with the accumulated dust 9, on the one hand, and a portion of the outer surface 1a of the pipe 1 corresponding to a portion of the inner surface 1b thereof, which is not in contact with the accumulated dust 9, in other words, corresponding to a vacant space 10 in the pipe 1, on the other hand.

As mentioned above the vacant space 10 in the pipe 1 has a thermal conductivity lower than that of the accumulated dust 9 in the pipe 1. Accordingly, because of the presence of the vacant space 10 having the lower thermal conductivity, a temperature of the portion of the outer surface 1a of the pipe 1 corresponding to the vacant space 10 decreases, under the effect of the above mentioned cooling, more rapidly than that of the portion of the outer surface 1a of the pipe 1 corresponding to the portion of the inner surface 1b thereof, which is in contact with the accumulated dust 9. As a result, the temperature $t_A$ of the portion of the outer surface 1a corresponding to the vacant space 10 is lower by ΔT than the temperature $t_N$ of the portion of the outer surface 1a corresponding to the portion of the inner surface 1b, which is in contact with the accumulated dust 9, after cooling for a certain period of time.

While the above mentioned difference in temperature ΔT still remains on the outer surface 1a of the pipe 1, the outer surface 1a of the pipe 1 is shot by means of a thermal imaging system 5 to obtain a thermal image of the difference in temperature ΔT, which has a portion showing a lower temperature, corresponding to the portion of the inner surface 1b of the pipe 1, which is not in contact with the accumulated dust 9, in other words, corresponding to the vacant space 10 in the pipe 1. The thus obtained thermal image is displayed on a monitor TV screen 6. It is therefore possible to detect a state of accumulation of the dust 9 in the pipe 1 by means of the above mentioned thermal image. More specifically, it is possible to detect a position, a shape and an approximate size of the vacant space 10 in the pipe 1 by means of the portion showing a lower temperature of the thermal image, and to detect the portion of the inner surface 1b of the pipe 1, which is in contact with the accumulated dust 9, by means of the portion showing a higher temperature of the thermal image. It is thus possible to detect a state of accumulation of the dust 9 in the pipe 1.

In the above mentioned fourth embodiment of the method of the present invention, by causing the accumulated dust 9 in the pipe 1 to contain previously hot water, it is possible to emphatically produce the above mentioned difference in temperature ΔT between the portion of the outer surface 1a of the pipe 1 corresponding to the portion of the inner surface 1b thereof, which is in contact with the accumulated dust 9, on the one hand, and the portion of the outer surface 1a of the pipe 1 corresponding to the portion of the inner surface 1b thereof, which is not in contact with the accumulated dust 9, in other words, corresponding to the vacant space 10 in the pipe 1, on the other hand. By shooting the outer surface 1a of the pipe 1 by means of the thermal imaging system 5 while the thus emphatically produced difference in temperature ΔT still remains on the outer surface 1a of the pipe, it is possible to detect more accurately the state of accumulation of the dust 9 in the pipe in the form of a further clearer thermal image showing the difference in temperature ΔT.

Figure 10:
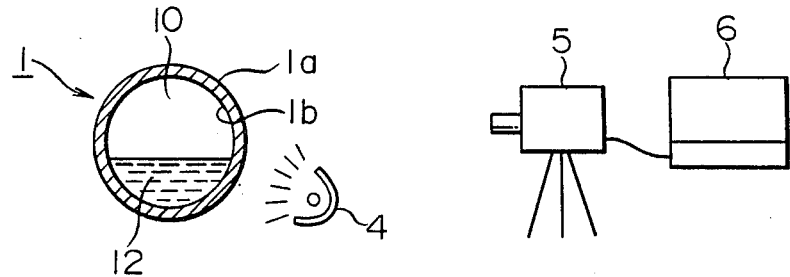
FIG. 10 is a schematic descriptive side view illustrating a fifth embodiment of the method of the present invention.

FIG. 10 is a schematic descriptive side view illustrating a fifth embodiment of the method of the present invention. As shown in FIG. 10, in the fifth embodiment of the method of the present invention, a pipe 1 to be tested, the outer surface 1a of which is exposed, is substantially horizontally arranged, and a liquid 12 as the aforementioned substance exists in the pipe 1. The pipe 1 is heated from the side of the outer surface 1a thereof by means of a heating mechanism 4 so that a difference in temperature is produced between a portion of the outer surface 1a of the pipe 1 corresponding to a portion of the inner surface 1b thereof, which is in contact with the existing liquid 12, on the one hand, and a portion of the outer surface 1a of the pipe 1 corresponding to a portion of the inner surface 1b thereof, which is not in contact with the existing liquid 12, in other words, corresponding to the vacant space 10 in the pipe 1, on the other hand.

The vacant space 10 in the pipe 1 has a thermal conductivity lower than that of the existing liquid 12 in the pipe 1. Accordingly, because of the presence of the vacant space 10 having the lower thermal conductivity, a temperature of the portion of the outer surface 1a of the pipe 1 corresponding to the vacant space 10 increases, under the effect of the above mentioned heating, more rapidly than that of the portion of the outer surface 1a of the pipe 1 corresponding to the portion of the inner surface 1b thereof, which is in contact with the existing liquid 12. As a result, the temperature $t_A$ of the portion of the outer surface 1a corresponding to the vacant space 10 is higher by ΔT than the temperature $t_N$ of the portion of the outer surface 1a corresponding to the portion of the inner surface 1b, which is in contact with the existing liquid 12, after heating for a certain period of time.

Figure 11:
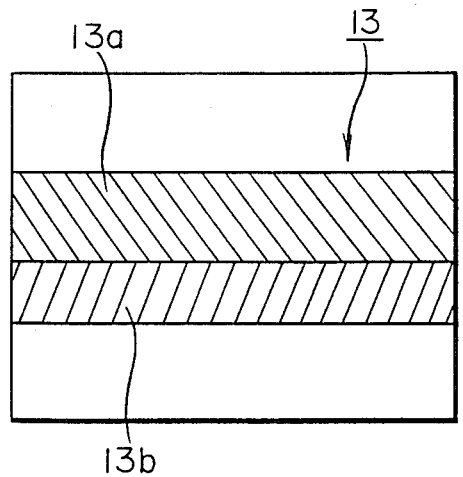
FIG. 11 is a descriptive view illustrating a typical thermal image shot in accordance with the fifth embodiment of the method of the present invention as shown in FIG. 10.

While the above mentioned difference in temperature ΔT still remains on the outer surface 1a of the pipe 1, the outer surface 1a of the pipe 1 is shot by means of a thermal imaging system 5 to obtain a thermal image of the difference in temperature ΔT, which has a portion showing a higher temperature, corresponding to the portion of the inner surface 1b of the pipe 1, which is not in contact with the existing liquid 12, in other words, corresponding to the vacant space 10 in the pipe 1. The thus obtained thermal image is displayed on a monitor TV screen 6. It is therefore possible to detect a level of the surface of the existing liquid 12 in the pipe 1 by means of the above mentioned thermal image. FIG. 11 is a descriptive view illustrating a typical thermal image 13 shot in the manner as described above. As shown in FIG. 11, the thermal image 13 of the outer surface 1a of the pipe 1 has a portion 13a showing a higher temperature, corresponding to the portion of the inner surface 1b of the pipe 1, which is not in contact with the existing liquid 12, in other words, corresponding to the vacant space 10 in the pipe 1, and a portion 13b showing a lower temperature, corresponding to the portion of the inner surface 1b of the pipe 1, which is in contact with the existing liquid 12. These portions 13a and 13b of the thermal image 13 are distinguishably indicated by colors predetermined for the respective ranges of temperature. More specifically, the portion 13a showing a relatively higher temperature is different in color from the portion 13b showing a relatively lower temperature. Therefore, it is possible to detect the vacant space 10 in the pipe 1 by means of the portion 13a showing a higher temperature of the thermal image 13 shown in FIG. 11, and to detect the portion of the inner surface 1b of the pipe 1, which is in contact with the existing liquid 12, by means of the portion 13b showing a lower temperature of the thermal image 13. It is thus possible to detect a level of the surface of the liquid 12 existing in the pipe 1.

Figure 12:
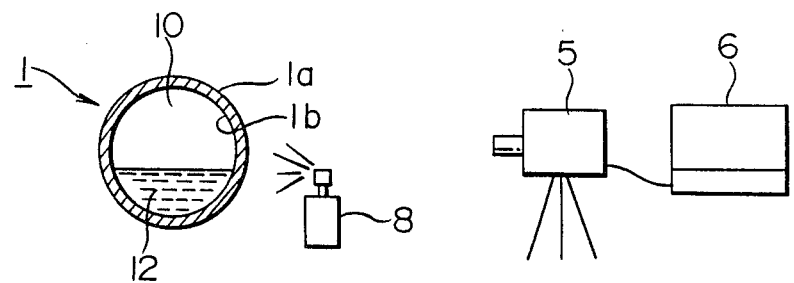
FIG. 12 is a schematic descriptive side view illustrating a sixth embodiment of the method of the present invention.

FIG. 12 is a schematic descriptive side view illustrating a sixth embodiment of the method of the present invention. As shown in FIG. 12, in the sixth embodiment of the method of the present invention, a pipe 1 to be tested, the outer surface 1a of which is exposed, is substantially horizontally arranged, and a liquid 12 as the aforementioned substance exists in the pipe 1. The pipe 1 is cooled from the side of the outer surface 1a thereof by means of a cooling mechanism 8 so that a difference in temperature is produced between a portion of the outer surface 1a of the pipe 1 corresponding to a portion of the inner surface 1b thereof, which is in contact with the existing liquid 12, on the one hand, and a portion of the outer surface 1a of the pipe 1 corresponding to a portion of the inner surface 1b thereof, which is not in contact with the existing liquid 12, in other words, corresponding to the vacant space 10 in the pipe 1, on the other hand.

As described above, the vacant space 10 in the pipe 1 has a thermal conductivity lower than that of the existing liquid 12 in the pipe 1. Accordingly, because of the presence of the vacant space 10 having the lower thermal conductivity, a temperature of the portion of the outer surface 1a of the pipe 1 corresponding to the vacant space 10 decreases, under the effect of the above mentioned cooling, more rapidly than that of the portion of the outer surface 1a of the pipe 1 corresponding to the portion of the inner surface 1b thereof, which is in contact with the existing liquid 12. As a result, the temperature $t_A$ of the portion of the outer surface 1a corresponding to the vacant space 10 is lower by ΔT than the temperature $t_N$ of the portion of the outer surface 1a corresponding to the portion of the inner surface 1b, which is in contact with the existing liquid 12, after cooling for a certain period of time.

While the above mentioned difference in temperature ΔT still remains on the outer surface 1a of the pipe 1, the outer surface 1a of the pipe 1 is shot by means of a thermal imaging system 5 to obtain a thermal image of the difference in temperature ΔT, which has a portion showing a lower temperature, corresponding to the portion of the inner surface 1b of the pipe 1, which is not in contact with the existing liquid 12, in other words, corresponding to the vacant space 10 in the pipe 1. The thus obtained thermal image is displayed on a monitor TV screen 6. It is therefore possible to detect a level of the surface of the existing liquid 12 in the pipe 1 by means of the above mentioned thermal image. More specifically, it is possible to detect the vacant space 10 in the pipe 1 by means of the portion showing a lower temperature of the thermal image, and to detect the portion of the inner surface 1b of the pipe 1, which is in contact with the existing liquid 12, by means of the portion showing a higher temperature of the thermal image. It is thus possible to detect a level of the surface of the liquid 12 existing in the pipe 1.

In the above mentioned fifth and sixth embodiments of the method of the present invention, when the liquid 12 existing in the pipe 1 has a temperature lower than the ambient temperature, it is desirable to heat the pipe 1 from the side of the outer surface 1a thereof in accordance with the fifth embodiment of the method of the present invention. When the liquid 12 existing in the pipe 1 has a temperature higher than the ambient temperature, on the other hand, it is desirable to cool the pipe 1 from the side of the outer surface 1a thereof in accordance with the sixth embodiment of the method of the present invention. According to the fifth and sixth embodiments of the method of the present invention, in a freezer, for example, it is possible to detect the boundary between the liquid phase and the gas phase of a cooling medium flowing through a pipe.

Figure 13:
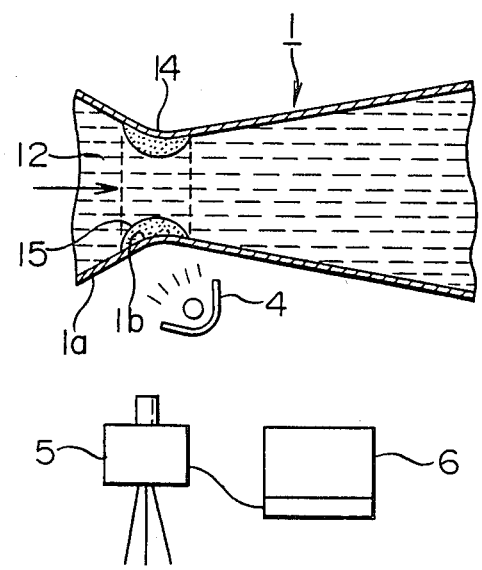
FIG. 13 is a schematic descriptive side view illustrating a seventh embodiment of the method of the present invention.

FIG. 13 is a schematic descriptive side view illustrating a seventh embodiment of the method of the present invention. As shown in FIG. 13, in the seventh embodiment of the method of the present invention, a pipe 1 to be tested, the outer surface 1a of which is exposed, has a neck portion 14 where the cross-sectional area of the pipe 1 is sharply reduced, and a liquid 12 as the aforementioned substance is flowing through the pipe 1 in the direction as indicated by the arrow. When the liquid 12 flowing through the pipe 1 passes through the neck portion 14, the flow velocity of the liquid 12 suddenly and remarkably increases. As a result, because of the abovementioned sudden and remarkable increase in the flow velocity of the liquid 12 at the neck portion 14 of the pipe 1, a cavity 15 is produced at the neck portion 14 of the pipe 1. For the purpose of detecting a position of occurrence of of the above mentioned cavity 15, the neck portion 14 of the pipe 1 is heated from the side of the outer surface 1a thereof by means of a heating mechanism 4 so that a difference in temperature is produced between a portion of the outer surface 1a of the pipe 1 corresponding to a portion of the inner surface 1b thereof, which is in contact with the flowing liquid 12, on the one hand, and a portion of the outer surface 1a of the pipe 1 corresponding to a portion of the inner surface 1b thereof at the neck portion 14, which is not in contact with the flowing liquid 12 under the effect of intervention of the above mentioned cavity 15, in other words, corresponding to the cavity 15 at the neck portion 14, on the other hand.

The cavity 15 at the neck portion 14 of the pipe 1 has a thermal conductivity lower than that of the flowing liquid 12 in the pipe 1. Accordingly, because of the presence of the cavity 15 having the lower thermal conductivity, a temperature of the portion of the outer surface 1a of the pipe 1 corresponding to the portion of the inner surface 1b thereof at the neck portion 14, which is not in contact with the flowing liquid 12, in other words, corresponding to the cavity 15 at the neck portion, increases, under the effect of the above mentioned heating, more rapidly than that of the portion of the outer surface 1a of the pipe 1 corresponding to the portion of the inner surface 1b thereof, which is in contact with the flowing liquid 12. As a result, the temperature $t_A$ of the portion of the outer surface 1a corresponding to the cavity 15 is higher by $\Delta T$ than the temperature $t_N$ of the portion of the outer surface 1a corresponding to the portion of the inner surface 1b, which is in contact with the flowing liquid 12, after heating for a certain period of time.

While the above mentioned difference in temperature $\Delta T$ still remains on the outer surface 1a of the pipe 1, the outer surface 1a of the pipe 1 at the neck portion thereof is shot by means of a thermal imaging system 5 to obtain a thermal image of the difference in temperature $\Delta T$, which has a portion showing a higher temperature, corresponding to the portion of the inner surface 1b of the pipe 1 at the neck portion 14 thereof, which is not in contact with the flowing liquid 12 under the effect of intervention of the cavity 15, in other words, corresponding to the cavity 15 at the neck portion 14. The thus obtained thermal image is displayed on a monitor TV screen 6. It is therefore possible to detect a position of occurrence and a magnitude of the cavity 15 at the neck portion 14 of the pipe 1 by means of the abovementioned thermal image.

Figure 14:
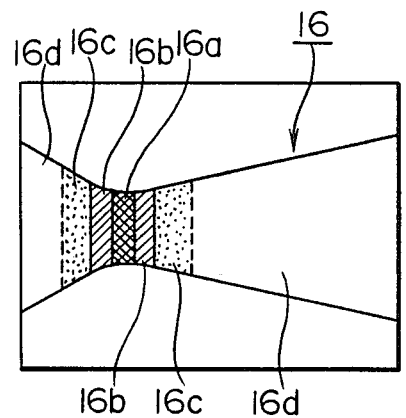
FIG. 14 is a descriptive view illustrating a typical thermal image shot in accordance with the seventh embodiment of the method of the present invention as shown in FIG. 13.

FIG. 14 is a descriptive view illustrating a typical thermal image 16 shot in the manner as described above. As shown in FIG. 14, the thermal image 16 of the outer surface 1a of the pipe 1 at the neck portion 14 thereof has portions 16a, 16b and 16c showing higher temperatures, corresponding to the portions of the inner surface 1b of the pipe 1 at the neck portion 14 thereof, which is not in contact with the flowing liquid 12 under the effect of intervention of the cavity 15, in other words, corresponding to the cavity 15 at the neck portion 14, and a portion 16d showing a lower temperature, corresponding to the portion of the inner surface 1b of the pipe 1, which is in contact with the flowing liquid 12. Among the portions 16a, 16b and 16c showing higher temperatures, the central portion 16a corresponding to the narrowest portion of the neck portion 14 shows the highest temperature, the outer portions 16b, 16b on the both sides of the central portion 16a show a high temperature next to that of the central portion 16a, and the outermost portions 16c, 16c on the both sides of the outer portions 16b, 16b show a high temperature next to that of the outer portions 16b, 16b. These portions 16a, 16b, 16c and 16d of the thermal image 16 are distinguishably indicated by colors predetermined for the respective ranges of temperature. More specifically, the portion showing a relatively higher temperature is different in color from the portion showing a relatively lower temperature. It is therefore possible to detect a position of occurrence and a magnitude of the cavity 15 at the neck portion 14 of the pipe 1 by means of the abovementioned portions 16a, 16b and 16c showing higher temperatures of the thermal image 16 shown in FIG. 14.

Figure 15:
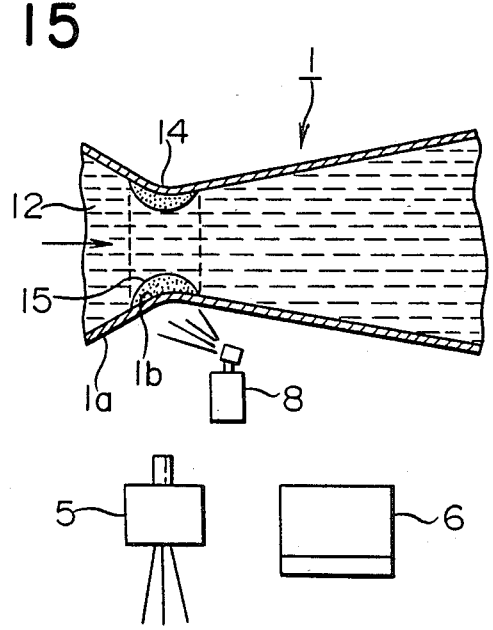
FIG. 15 is a schematic descriptive side view illustrating an eighth embodiment of the method of the present invention.

FIG. 15 is a schematic descriptive side view illustrating an eighth embodiment of the method of the present invention. As shown in FIG. 15, in the eighth embodiment of the method of the present invention, a pipe 1 to be tested, the outer surface 1a of which is exposed, has a neck portion 14 where the cross-sectional area of the pipe 1 is sharply reduced, and a liquid 12 as the aforementioned substance is flowing through the pipe 1 in the direction as indicated by the arrow. When the liquid 12 flowing through the pipe 1 passes through the neck portion 14, the flow velocity of the liquid 12 suddenly remarkably increases. As a result, because of the above mentioned sudden and remarkable increase in the flow velocity of the liquid 12 at the neck portion 14 of the pipe 1, a cavity 15 is produced at the neck portion 14 of the pipe 1 as described above. For the purpose of detecting a position of occurrence of the above mentioned cavity 15, the neck portion 14 of the pipe 1 is cooled from the side of the outer surface 1a thereof by means of a cooling mechanism 8 so that a difference in temperature is produced between a portion of the outer surface 1a of the pipe 1 corresponding to a portion of the inner surface 1b thereof, which is in contact with the flowing liquid 12, on the one hand, and a portion of the outer surface 1a of the pipe 1 corresponding to a portion of the inner surface 1b thereof at the neck portion 14, which is not in contact with the flowing liquid 12 under the effect of intervention of the above mentioned cavity 15, in other words, corresponding to the cavity 15 at the neck portion 14, on the other hand.

As described above, the cavity 15 at the neck portion 14 of the pipe 1 has a thermal conductivity lower than that of the flowing liquid 12 in the pipe 1. Accordingly, because of the presence of the cavity 15 having the lower thermal conductivity, a temperature of the portion of the outer surface 1a of the pipe 1 corresponding to the portion of the inner surface 1b thereof at the neck portion 14, which is not in contact with the flowing liquid 12, in other words, corresponding to the cavity 15 at the neck portion, decreases, under the effect of the above mentioned cooling, more rapidly than that of the portion of the outer surface 1a of the pipe 1 corresponding to the portion of the inner surface 1b thereof, which is in contact with the flowing liquid 12. As a result, the temperature $t_A$ of the portion of the outer surface 1a corresponding to the cavity 15 is lower by $\Delta T$ than the temperature $t_N$ of the portion of the outer surface 1a corresponding to the portion of the inner surface 1b, which is in contact with the flowing liquid 12, after cooling for a certain period of time.

While the above mentioned difference in temperature $\Delta T$ still remains on the outer surface 1a of the pipe 1, the outer surface 1a of the pipe 1 at the neck portion thereof is shot by means of a thermal imaging system 5 to obtain a thermal image of the difference in temperature $\Delta T$, which has a portion showing a lower temperature, corresponding to the portion of the inner surface 1b of the pipe 1 at the neck portion 14 thereof, which is not in contact with the flowing liquid 12 under the effect of intervention of the cavity 15, in other words, corresponding to the cavity 15 at the neck portion 14. The thus obtained thermal image is displayed on a monitor TV screen 6. It is therefore possible to detect a position of occurrence and a magnitude of the cavity 15 at the neck portion 14 of the pipe 1 by means of the abovementioned thermal image. More particularly, it is possible to detect a position of occurrence and a magnitude of the cavity 15 at the neck portion 14 of the pipe 1 by means of the portions showing lower temperatures of the thermal image.

In the above mentioned seventh and eighth embodiments of the method of the present invention, when the liquid 12 flowing through the pipe 1 has a temperature lower than the ambient temperature, it is desirable to heat the neck portion 14 of the pipe 1 from the side of the outer surface 1a thereof in accordance with the abovementioned seventh embodiment of the method of the present invention. When the liquid 12 flowing through the pipe 1 has a temperature higher than the ambient temperature, on the other hand, it is desirable to cool the neck portion 14 of the pipe 1 from the side of the outer surface 1a thereof in accordance with the above mentioned eighth embodiment of the method of the present invention.

In the above mentioned first to eighth embodiments of the method of the present invention, a state of a solid or liquid substance existing in the pipe 1 may be detected over the entire circumference of the inner surface 1b of the pipe 1 by sequentially shooting the outer surface 1a of the pipe 1 by means of the thermal imaging system 5 from a plurality of spots in the circumferential direction of the pipe 1.

In the first to eighth embodiments of the method of the present invention, the material of the pipe 1 to be tested, in which a solid or liquid substance exists, may be any of a metal such as steel, plastics, concrete or any other material. The method of the present invention is applicable to any cross-sectional shape and size of the pipe 1 to be tested. A solid substance existing in the pipe 1 may be any substance, not limited to concrete 2 and dust 9, and a liquid substance existing in the pipe 1 may be water or any other liquid. In addition, the method of the present invention is applicable to, for example, detection of a state of any of the above mentioned substances existing in a container, not limited to detection of a state of a solid or liquid substance existing in the pipe 1.

According to the method of the present invention, as described above in detail, the following industrially useful effects are provided:

(1) By shooting the outer surface of a pipe to be tested by means of a thermal imaging system, a state of a substance existing in the pipe is instantaneously displayed on a monitor TV screen. It is therefore possible to certainly, easily and efficiently detect a state of the substance existing in the pipe.

(2) It is possible to detect a state of a substance existing in a pipe to be tested in a non-contact manner at a position apart from the pipe. It is not therefore necessary to provide a scaffold for detecting operation even when the pipe is installed at an elevated position apart from the ground.

(3) Handling of a thermal imaging system does not require a special qualification. There is therefore no limitation in personnel.

(4) The range of a single run of detection of a state of a substance existing in a pipe to be tested is wider than that for the conventional detecting methods, thus providing a higher operating efficiency.

(5) A state of a substance existing even in a pipe in service may be detected.

(6) For a pipe, having a neck portion where the cross-sectional area of the pipe is sharply reduced, and through which a liquid is flowing, it is possible to accurately detect a position of occurrence and a magnitude of a cavity at the neck portion. Furthermore, smooth flow of the liquid through the pipe is never impaired, since it is not necessary to install an underwater microphone in the pipe as in the conventional detection of the cavity.

What is claimed is:

1. A method for detecting a position of occurrence of a cavity at a neck portion of a pipe, the outer surface of which is exposed, comprising:

heating a pipe having a neck portion where the cross-sectional area of said pipe is sharply reduced, the outer surface of which is exposed, from the side of the outer surface thereof so that a difference in temperature is produced between a portion of the outer surface of said pipe corresponding to a portion of the inner surface thereof, which is in contact with a liquid flowing through said pipe, and a portion of the outer surface of said pipe corresponding to a portion of the inner surface thereof at said neck portion, which is not in contact with said flowing liquid under the effect of intervention of a cavity caused by a sudden increase in flow velocity of said liquid passing through said neck portion; then shooting the outer surface of said pipe by means of a thermal imaging system while said difference in temperature still remains on the outer surface of said pipe to obtain a thermal image of said difference in temperature, which has a portion showing a higher temperature, corresponding to the portion of the inner surface of said pipe, which is not in contact with said flowing liquid; and detecting a position of occurrence of said cavity at said neck portion of said pipe by means of said thermal image thus obtained.

2. A method for detecting a position of occurrence of a cavity at a neck portion of a pipe, the outer surface of which is exposed, comprising:

cooling a pipe having a neck portion where the cross-sectional area of said pipe is sharply reduced, the outer surface of which is exposed, from the side of the outer surface thereof so that a difference in temperature is produced between a portion of the outer surface of said pipe corresponding to a portion of the inner surface thereof, which is in contact with a liquid flowing through said pipe, and a portion of the outer surface of said pipe corresponding to a portion of the inner surface thereof at said neck portion, which is not in contact with said flowing liquid under the effect of intervention of a cavity caused by a sudden increase in flow velocity of said liquid passing through said neck portion; then shooting the outer surface of said pipe by means of a thermal imaging system while said difference in temperature still remains on the outer surface of said pipe to obtain a thermal image of said difference in temperature, which has a portion showing a lower temperature, corresponding to the portion of the inner surface of said pipe, which is not in contact with said flowing liquid; and detecting a position of occurrence of said cavity at said neck portion of said pipe by means of said thermal image thus obtained.

3. A method for detecting a state of charging of concrete in a pipe, the outer surface of which is exposed, comprising:

heating a pipe, the outer surface of which is exposed, from the side of the outer surface thereof so that a difference in temperature is produced between a portion of the outer surface of said pipe corresponding to a portion of the inner surface thereof, which is in contact with concrete charged in said pipe, and a portion of the outer surface of said pipe corresponding to a portion of the inner surface thereof, which is not in contact with said charged concrete; then shooting the outer surface of said pipe by means of a thermal imaging system while said difference in temperature still remains on the outer surface of said pipe to obtain a thermal image of said difference in temperature, which has a portion showing a higher temperature, corresponding to the portion of the inner surface of said pipe, which is not in contact with said charged concrete; and detecting a state of charging of said concrete in said pipe by means of said thermal image thus obtained.

4. A method for detecting a state of charging of concrete in a pipe, the outer surface of which is exposed, comprising:

cooling a pipe, the outer surface of which is exposed, from the side of the outer surface thereof so that a difference in temperature is produced between a portion of the outer surface of said pipe corresponding to a portion of the inner surface thereof, which is in contact with concrete charged in said pipe, and a portion of the outer surface of said pipe corresponding to a portion of the inner surface thereof, which is not in contact with said charged concrete; then shooting the outer surface of said pipe by means of a thermal imaging system while said difference in temperature still remains on the outer surface of said pipe to obtain a thermal image of said difference in temperature, which has a portion showing a lower temperature, corresponding to the portion of the inner surface of said pipe, which is not in contact with said charged concrete; and detecting a state of charging of said concrete in said pipe by means of said thermal image thus obtained.

5. A method for detecting a level of the surface of a liquid existing in a pipe, the outer surface of which is exposed, comprising:

heating a pipe, the outer surface of which is exposed, from the side of the outer surface thereof so that a difference in temperature is produced between a portion of the outer surface of said pipe corresponding to a portion of the inner surface thereof, which is in contact with a liquid existing in said pipe, and a portion of the outer surface of said pipe corresponding to a portion of the inner surface thereof, which is not in contact with said existing liquid; then shooting the outer surface of said pipe by means of a thermal imaging system while said difference in temperature still remains on the outer surface of said pipe to obtain a thermal image of said difference in temperature, which has a portion showing a higher temperature, corresponding to the portion of the inner surface of said pipe, which is not in contact with said existing liquid; and detecting a level of the surface of said existing liquid in said pipe by means of said thermal image thus obtained.

6. A method for detecting a level of the surface of a liquid existing in a pipe, the outer surface of which is exposed, comprising:

cooling a pipe, the outer surface of which is exposed, from the side of the outer surface thereof so that a difference in temperature is produced between a portion of the outer surface of said pipe corresponding to a portion of the inner surface thereof, which is in contact with a liquid existing in said pipe, and a portion of the outer surface of said pipe corresponding to a portion of the inner surface thereof, which is not in contact with said existing liquid; then shooting the outer surface of said pipe by means of a thermal imaging system while said difference in temperature still remains on the outer surface of said pipe to obtain a thermal image of said difference in temperature, which has a portion showing a lower temperature, corresponding to the portion of the inner surface of said pipe, which is not in contact with said existing liquid; and detecting a level of the surface of said existing liquid in said pipe by means of said thermal image thus obtained.

* * * * *